(12) United States Patent
Sheth (10) Patent No.: US 10,238,561 B2
(45) Date of Patent: *Mar. 26, 2019

(54) SYSTEM AND METHOD FOR TREATING AND PREVENTING PRESSURE SORES IN BEDRIDDEN PATIENTS

(71) Applicant: Piyush Sheth, Porter Ranch, CA (US)

(72) Inventor: Piyush Sheth, Porter Ranch, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/921,942

(22) Filed: Mar. 15, 2018

(65) Prior Publication Data

US 2018/0369041 A1 Dec. 27, 2018

Related U.S. Application Data

(63) Continuation-in-part of application No. 15/639,895, filed on Jun. 30, 2017.

(Continued)

(51) Int. Cl.
*A61G 7/05* (2006.01)
*A47C 27/08* (2006.01)
(Continued)

(52) U.S. Cl.
CPC ........ *A61G 7/05776* (2013.01); *A47C 27/083* (2013.01); *A61B 5/1036* (2013.01);
(Continued)

(58) Field of Classification Search
CPC .............. A61G 7/05576; A61G 7/0005; A47C 27/083; A61B 5/1036; A61B 5/6892
See application file for complete search history.

(56) References Cited

U.S. PATENT DOCUMENTS

| 3,302,219 A | 2/1967 | Harris |
| 3,605,145 A * | 9/1971 | Graebe ................ A47C 27/081 297/DIG. 3 |

(Continued)

FOREIGN PATENT DOCUMENTS

| CN | 105362059 A | 3/2016 |
| EP | 2047831 A1 | 4/2009 |

OTHER PUBLICATIONS

ROHO PRODIGY Mattress System—Inflatable Mattress Overlay Air Cushion retrieved from the Internet URL https://www.exmed.net/p-2089-roho-prodigy-mattress-system-inflatable-mattress-overlay-air-cushion.aspx?defaultvariantid=21007&gclid=cozurbl57dqcfynpfgoddu0d9q on Jul. 5, 2017.

(Continued)

*Primary Examiner* — Eric J Kurilla
(74) *Attorney, Agent, or Firm* — Procopio Cory Hargreaves and Savitch LLP (57) ABSTRACT

A system for preventing and treating pressure sores of a bed-ridden patient including an array of expandable and collapsible supports to support and provide pressure relief to a patient in pressure locations where the expandable and collapsible supports support the patient; pressure sensors associated with the expandable and collapsible supports to monitor pressure locations where the expandable and collapsible supports support the patient; and a patient lift movable between the expandable and collapsible supports to raise and lower the patient between at least a position where the patient is primarily supported by the array of expandable and collapsible supports and a position above the expandable and collapsible supports where the patient is primarily supported by the patient lift.

16 Claims, 11 Drawing Sheets

Related U.S. Application Data (60) Provisional application No. 62/523,261, filed on Jun. 22, 2017.

(51) Int. Cl.
*A61G 7/10* (2006.01)
*A61G 7/057* (2006.01)
*A61B 5/00* (2006.01)
*A61B 5/103* (2006.01)

(52) U.S. Cl.
CPC .......... *A61B 5/6892* (2013.01); *A61G 7/1021* (2013.01); *A61G 2203/34* (2013.01)

(56) References Cited

U.S. PATENT DOCUMENTS

| | | | |
|---|---|---|---|
| 3,893,198 A | 7/1975 | Blair | |
| 4,542,547 A | 9/1985 | Sato | |
| 4,653,130 A | 3/1987 | Senoue et al. | |
| 5,025,515 A * | 6/1991 | Rhines | A47K 3/06 4/584 |
| 5,173,978 A | 12/1992 | Kassai et al. | |
| 5,192,304 A * | 3/1993 | Rassman | A61H 9/0078 5/933 |
| 5,235,712 A | 8/1993 | Smith | |
| 5,239,713 A | 8/1993 | Toivio et al. | |
| 5,341,820 A | 8/1994 | Hammett | |
| 5,446,933 A * | 9/1995 | Gabelhouse | A47C 23/002 5/670 |
| 5,487,196 A | 1/1996 | Wilkinson et al. | |
| 5,704,083 A * | 1/1998 | Nerg | A61G 7/0005 5/600 |
| 6,212,719 B1 * | 4/2001 | Thomas | A47C 4/54 297/284.6 |
| 6,487,738 B1 * | 12/2002 | Graebe | A47C 23/043 267/82 |
| 6,560,803 B2 * | 5/2003 | Zur | A61G 5/1043 297/284.6 |
| 6,581,225 B1 * | 6/2003 | Imai | A61G 7/057 5/421 |
| 6,823,549 B1 * | 11/2004 | Hampton | A61G 7/05776 297/284.6 |
| 6,829,797 B2 * | 12/2004 | Partian | A61G 7/057 5/710 |
| 6,859,967 B2 | 3/2005 | Harrison et al. | |
| 7,013,511 B2 | 3/2006 | Maschke | |
| 7,520,011 B1 * | 4/2009 | Liberkowski | A47C 23/002 5/719 |
| 8,528,135 B2 | 9/2013 | Turo et al. | |
| 8,752,222 B2 | 6/2014 | Papaioannou | |
| 8,863,338 B2 * | 10/2014 | Dzioba | A61G 7/05776 5/655.3 |
| 9,333,136 B2 | 5/2016 | Gibson et al. | |
| 9,591,995 B2 * | 3/2017 | Blumberg | A47C 23/002 |
| 2001/0039681 A1 | 11/2001 | Johnson et al. | |
| 2004/0045090 A1 * | 3/2004 | Tsai | A47C 27/084 5/709 |
| 2006/0085919 A1 * | 4/2006 | Kramer | A47C 27/082 5/713 |
| 2006/0112489 A1 * | 6/2006 | Bobey | A61B 5/1115 5/655.3 |
| 2011/0061159 A1 * | 3/2011 | Mardirossian | A47K 3/282 4/611 |
| 2011/0239370 A1 | 10/2011 | Turo et al. | |
| 2011/0314611 A1 | 12/2011 | Thomas | |
| 2013/0061385 A1 * | 3/2013 | Al-Madi | A61G 7/0005 4/546 |
| 2014/0041127 A1 | 2/2014 | Codos | |
| 2014/0310875 A1 | 10/2014 | Kazuyoshi et al. | |
| 2015/0026895 A1 | 1/2015 | Geelen et al. | |

OTHER PUBLICATIONS

Buhr, Sarah, "Purple, a Utah mattress startup you've probably never heard of, is on track to unicorndom", Tech Crunch, posted Apr. 13, 2017, retrieved from the Internet URL https://techcrunch.com/2017/04/13/purple-a-utah-mattress-startup-youve-probably-never-heard-of-is-on-track-to-unicorndom/ on Jul. 5, 2017.

International Search Report and Written Opinion for International Patent Application No. PCT/US2018/036124 dated Nov. 6, 2018 in 14 pages.

* cited by examiner

SYSTEM AND METHOD FOR TREATING AND PREVENTING PRESSURE SORES IN BEDRIDDEN PATIENTS

CROSS-REFERENCE TO RELATED APPLICATIONS

This application is a continuation-in-part of U.S. Non-provisional patent application Ser. No. 15/639,895, filed on Jun. 30, 2017, and claims priority to U.S. Provisional Patent Application No. 62/523,261, filed on Jun. 22, 2017, both of which are incorporated by reference herein.

FIELD OF THE INVENTION

The present invention relates to systems and methods for treating and preventing pressure sores in bedridden patients.

BACKGROUND OF THE INVENTION

Currently there are a number of attempts for treating pressure sores like air-loss beds and pressure mapping systems. Some of these attempts map the pressure on the back of the patient body but these solutions fail to prevent and/or treat pressure sores. Other attempts try to reduce pressure, but these solutions do not relieve the pressure points on the patients back especially the sacral layers and the heels/ankles. None of these attempts seek to address how to increase the oxygenation in the sore areas.

It would be desirable to have a pressure monitoring bed which will enable mapping of the pressure on the patient body. Furthermore, it would also be desirable to have ability to reduce pressure at sore points. This reduction in pressure at one location will cause the high pressure point to shift to a different location. But if there is an easy system to keep alternating high pressure points between different locations along with total pressure relief by elevation, oxygenation and water massage with ability to clean the patient's back dry and apply topical moisturizers etc., would prevent sores. Furthermore, it would also be desirable to have mechanics in the bed to raise the patient to clean his back. Still further, it would be desirable to provide oxygenation and massage the back of the patient body. Therefore, there currently exists a need in the industry for a therapeutic surface for chronically ill patients to prevent and treat pressure sores.

SUMMARY OF THE INVENTION

An aspect of the invention involves a therapeutic surface for chronically ill patients to prevent and treat pressure sores. Patient can be any patient who is immobile and bedridden due to any chronic illness or in coma. The therapeutic surface includes horizontal and vertical rows of balloons with embedded pressure sensors, rods with holes for oxygenation and water-jets, pneumatic actuators and a pressure mapping system to monitor pressure. These components are connected as follows—the array of balloons forms an unstitched mattress when the patient rests on it and allows for monitoring of pressure in each balloon allowing adjustment of the pressure in the balloon as required. The horizontal rods lay within the array of balloons to allow aeration/oxygenation and water jet massage of the back of the patient body through the interstitial space between the balloons.

The device may also have one or more of the following: ability to lift the entire patient body or the torso-alone or the lower extremities to enable relieving pressure in respective areas and enable better cleaning and drying of the patient body for good hygiene.

Another aspect of the invention involves a therapeutic surface with the capability to monitor and alleviate the pressure points and provides air/oxygen and water jets to prevent and treat bed sores in bed-ridden patients. An array of balloons touching each other form a mattress of unstitched but contiguous balloons like in a conventional mattress with stitched puffs. Individual pressure sensors placed within each balloon measure and monitor pressure. Furthermore, horizontal rods which lay between the balloons perform oxygenation and provide water massage to the back of the patient body from the interstitial spaces within the unstitched mattress of contiguous balloons. The rods are raised to raise the patient above the mattress to relieve overall pressure and enable cleaning and wipe down of the back of the patient body. The rods can raise the entire patient body or its torso alone or the lower extremities alone to clean as desired.

A further aspect of the invention involves a system for preventing and treating pressure sores of a patient. The system includes an array of expandable and collapsible supports to support and provide pressure relief to a patient in pressure locations where the expandable and collapsible supports support the patient; pressure sensors associated with the expandable and collapsible supports to monitor pressure locations where the expandable and collapsible supports support the patient; a patient lift movable between the expandable and collapsible supports to raise one or more areas of the patient, the patient lift including one or more dry-air, controlled-humidity air, and/or oxygen emitters to oxygenate/aerate one or more areas of the patient.

One or more implementations of the aspect of the invention described immediately above includes one or more of the following: the system is a hospital bed; the system is a seat; the lift includes multiple actuators that raise the patient to clean a back of the patient; the lift includes one or more water emitters to massage one or more areas of a back of the patient's back; the array of expandable and collapsible supports include interstitial spaces between the balloons and the one or more dry-air, controlled-humidity air, and/or oxygen emitters are disposed in the interstitial spaces to emit oxygen/air through to oxygenate/aerate one or more areas of the patient's back; the expandable and collapsible supports provide pressure relief and the one or more dry-air, controlled-humidity air, and/or oxygen emitters provide oxygenation without elevating the patient with the patient lift; the expandable and collapsible supports are inflatable balloons; the inflatable balloons are embedded with the pressure sensors; the lift includes horizontal rods disposed between the expandable and collapsible supports, and the horizontal rods include the one or more dry-air, controlled-humidity air, and/or oxygen emitters; and/or the lift includes one or more hinges, enabling the lift to lift one or more of the patient's torso alone, the patient's lower extremities alone, and the patient's entire body.

A still further aspect of the invention involves a method of preventing and treating pressure sores of a patient using the system described above. The method includes monitoring pressure in the expandable and collapsible supports using the pressure sensors; at least partially collapsing one or more expandable and collapsible supports based on the pressure in the expandable and collapsible supports to provide pressure relief to the patient in the pressure locations where the expandable and collapsible supports support the patient and the pressure is high; and oxygenating one or more areas of the patient with the one or more dry-air, controlled-humidity air, and/or oxygen emitters of the patient lift.

One or more implementations of the aspect of the invention described immediately above includes one or more of the following: the lift includes one or more water emitters to massage one or more areas of a back of the patient, and the method includes irrigating one or more areas of the back of the patient with the one or more water emitters of the patient lift; the array of expandable and collapsible supports include interstitial spaces between the balloons and the one or more water emitters are disposed in the interstitial spaces, and irrigation includes irrigating through the interstitial spaces the one or more areas of the back of the patient; the array of expandable and collapsible supports include interstitial spaces between the balloons and the one or more dry-air, controlled-humidity air, and/or oxygen emitters are disposed in the interstitial spaces, and the method includes emitting air/oxygen through the interstitial spaces to oxygenate/aerate one or more areas of the patient; and/or moving the patient lift between the expandable and collapsible supports to raise one or more areas of the patient.

Another aspect of the invention involves a system for preventing and treating pressure sores of a patient including an array of expandable and collapsible supports to support and provide pressure relief to a patient in pressure locations where the expandable and collapsible supports support the patient; pressure sensors associated with the expandable and collapsible supports to monitor pressure locations where the expandable and collapsible supports support the patient; and a patient lift movable between the expandable and collapsible supports to raise and lower the patient between at least a position where the patient is primarily supported by the array of expandable and collapsible supports and a position above the expandable and collapsible supports where the patient is primarily supported by the patient lift.

One or more implementations of the aspect of the invention described immediately above includes one or more of the following: the patient lift includes a plurality of holes, one hole per expandable and collapsible support, that the expandable and collapsible supports are respectively disposed within when the patient lift is raised and lowered; the patient lift is a top mattress; the patient lift is an air-filled mattress; the system is integrated into a hospital bed; the system is integrated into a seat that is a member of the group consisting of wheel chair seating, seats in automobiles, airplanes, workplace seats in factories and offices, and back massage chairs; the lift includes multiple actuators operably associated with the patient lift to raise and lower the patient lift; a bottom air filled mattress with the array of expandable and collapsible supports; the expandable and collapsible supports are inflatable balloons; pressure sensors are respectively associated with the inflatable balloons, and further including a controller operably associated with the pressure sensors and the inflatable balloons to control the inflation of the inflatable balloons based on the sensed pressure by the pressure sensors to prevent pressure sores; dry-air, controlled-humidity air, and/or dry-air, controlled-humidity air, and/or oxygen emitters for application to one or more areas of the patient; one or more water emitters to at least massage one or more areas and wash one or more areas of the patient.

Another embodiment of the invention involves a method of preventing and treating pressure sores of a patient using the system described immediately above, comprising: moving the patient lift movable between the expandable and collapsible supports to raise and lower the patient between at least a position where the patient is primarily supported by the array of expandable and collapsible supports and a position above the expandable and collapsible supports where the patient is primarily supported by the patient lift.

In an implementation of the aspect of the invention described immediately above the patient lift includes a plurality of holes, one hole per expandable and collapsible support, and moving the patient lift includes moving the patient lift so that that the expandable and collapsible supports are respectively disposed within the plurality of holes, one hole per expandable and collapsible support, while the patient lift is raised and lowered over the expandable and collapsible supports.

In an implementation of the aspect of the invention described immediately above, where the system is a hospital bed, the expandable and collapsible supports are balloons that touch adjacent balloons on all sides upon inflation, so that it makes a nice puffed contiguous mattress except that the puffs are unstitched unlike in a typical mattress. When the balloons are slightly deflated, they don't touch adjacent balloons and therefore allow easy lifting of the top mattress/patient lift.

The invention will now be described more fully hereinafter with reference to the accompanying drawings, which are intended to be read in conjunction with both this summary, the detailed description and any preferred and/or particular embodiments and variations specifically discussed or otherwise disclosed. This invention may, however, be embodied in many different forms and should not be construed as limited to the embodiments set forth herein; rather, these embodiments are provided by way of illustration only and so that this disclosure will be thorough, complete and fully conveys the full scope of the invention to those skilled in the art.

BRIEF DESCRIPTION OF DRAWINGS

The accompanying drawings, which are incorporated in and form a part of this specification illustrate embodiments of the invention and together with the description, serve to explain the principles of the invention.

DESCRIPTION OF EMBODIMENT OF THE INVENTION

Figure 1:
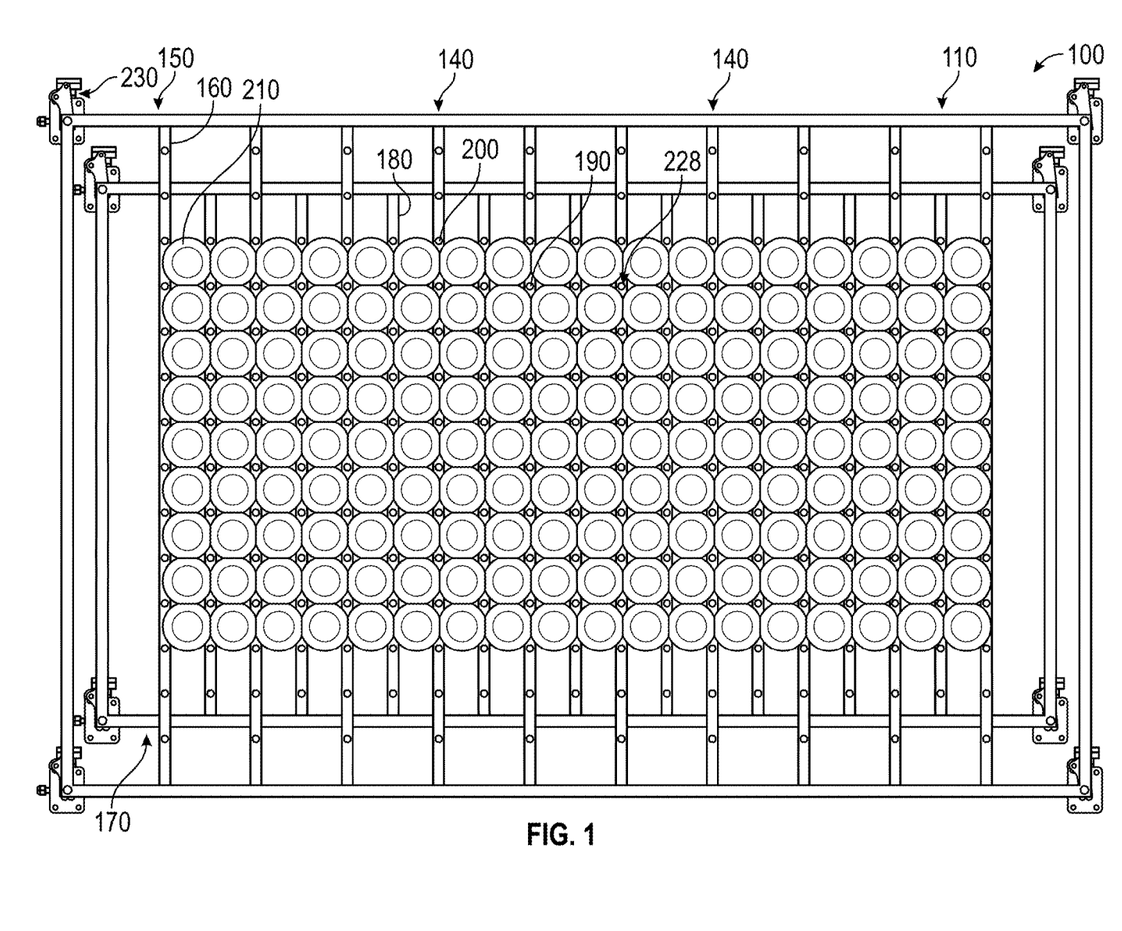
FIG. 1 is a top view of an embodiment of a system for treating and preventing pressure sores in bedridden patients.
Figure 2:
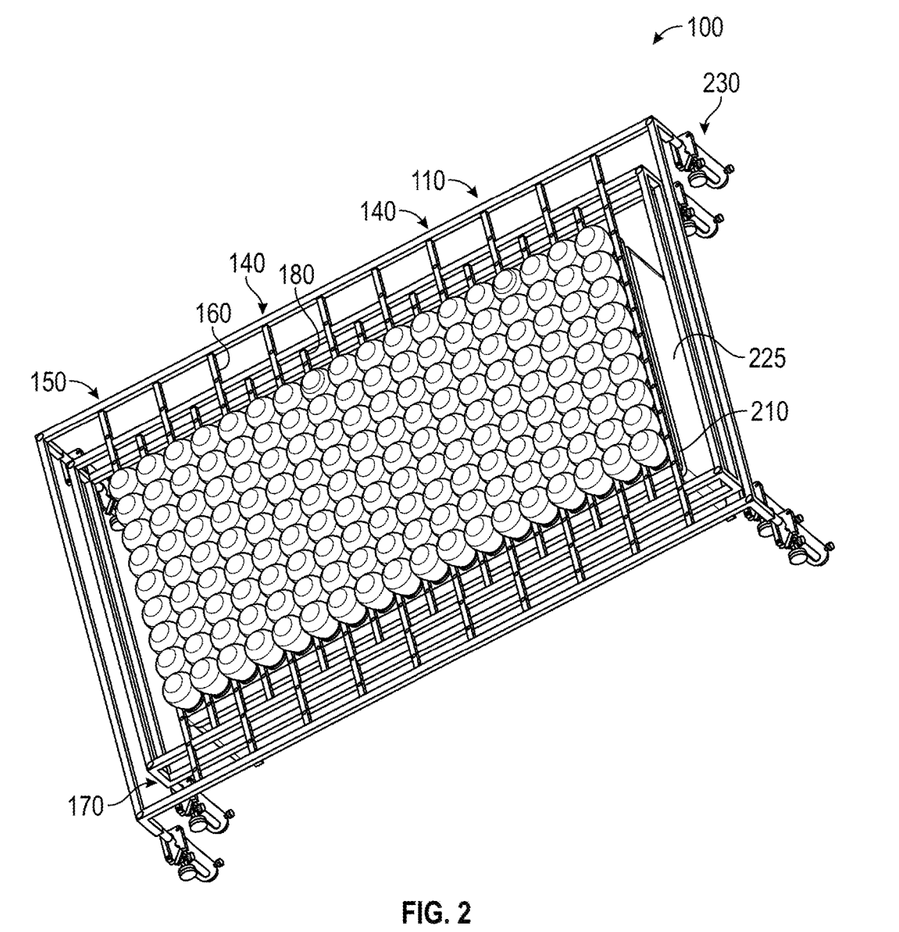
FIG. 2 is a perspective view of the system of FIG. 1.
Figure 4:
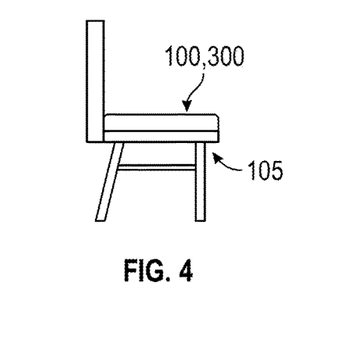
FIG. 4 is a block diagram illustrating an embodiment of a seat incorporating the system of FIG. 1.

With reference to FIGS. 1-2, an embodiment of a therapeutic surface or system 100 for treating and preventing pressure sores in bedridden patients will be described. Although the system 100 is shown and described as a unique hospital bed, one or more features of the system 100 may be implemented in other types of beds, other therapeutic surfaces, other support surfaces, and/or other types of seats 105 (FIG. 4) such as, but not limited to, wheel chair seating, seats in automobiles, airplanes, workplace seats in factories and offices, back massage chairs.

The therapeutic surface/system 100 includes a movable support frame assembly 110 including an outer support frame assembly 150 resting on the slots of the inner support frame assembly 170. Both the outer and inner support frame assemblies 150, 170 have two hinge/pivot points 140 along the length of the frames to lift the torso and the lower extremities. The hinge/pivot points 140 will have structural vertical supports (not shown) under the hinge/pivot points 140. The rectangular outer support frame 150 includes rods 160 spanning laterally across the rectangular outer support frame 150 and evenly spaced in along the length of the rectangular outer support frame 150. The rectangular inner support frame 170 includes rods 180 spanning laterally across the rectangular inner support frame 170 and evenly spaced in along the length of the rectangular inner support frame 170.

The rods 160, 180 include emitters/holes 190, 200 for oxygenation/dry aeration/controlled humidity aeration and water-jets, respectively. The emitters/holes 190, 200 alternate (e.g., air/oxygen, water, air/oxygen, water, etc.).

Figure 13:
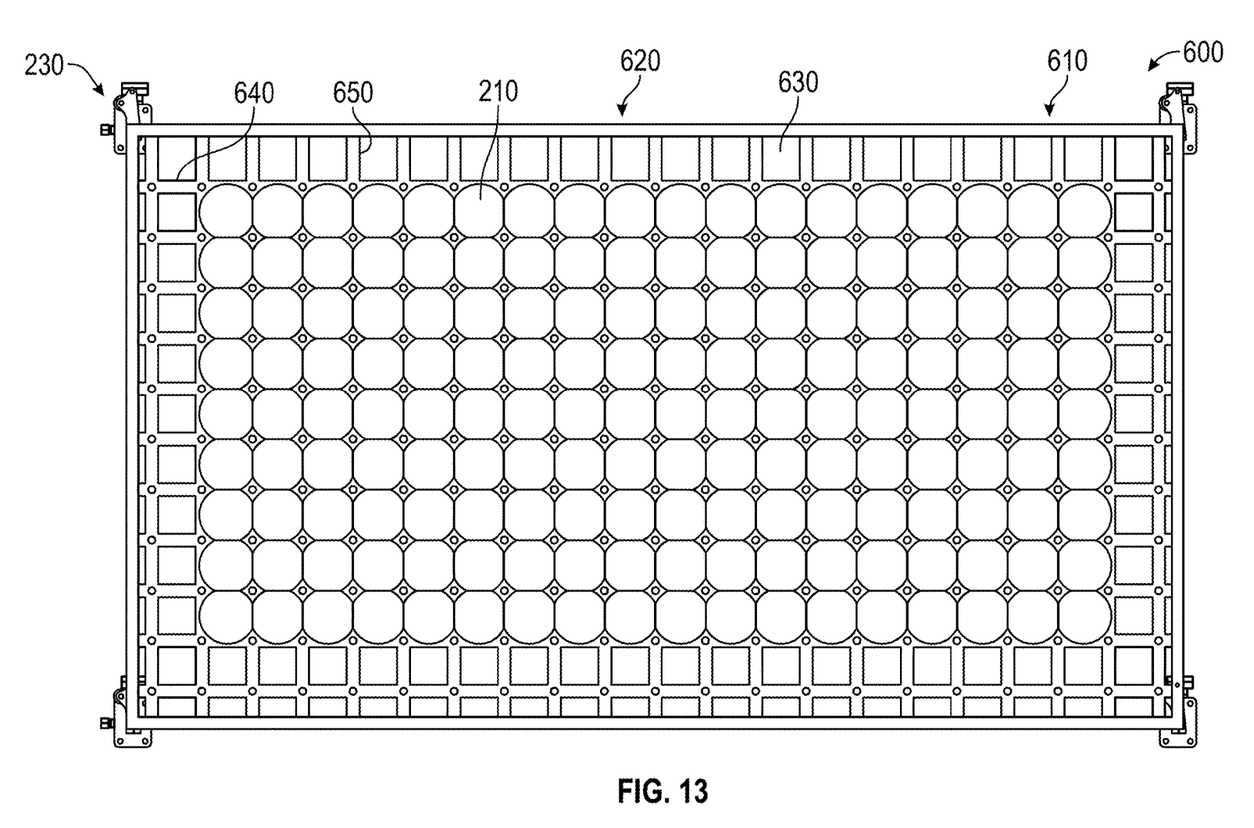
FIG. 13 is a top plan view of another embodiment of a system for treating and preventing pressure sores in bedridden patients.
Figure 14:
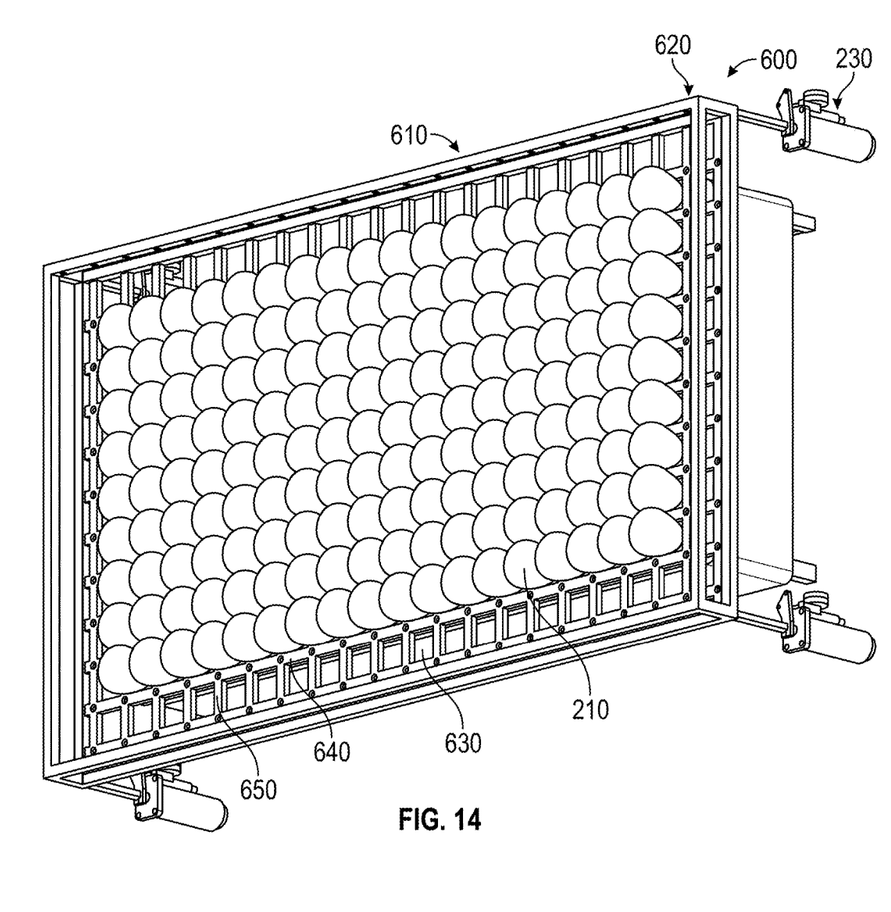
FIG. 14 is a perspective view of the system shown in FIG. 13.

Alternatively, in another embodiment of a therapeutic surface or system 600 for treating and preventing pressure sores in bedridden patients, as shown in FIGS. 13 and 14, a movable support frame assembly 610 includes a grill-like frame 620 with a plurality of rectangular holes 630 and longitudinal/horizontal rods 640, 650 to lift the patient. Actuators 230 raise/lower the movable support frame assembly 610 and patient relative to balloons 210.

Alternatively, the movable support frame assembly 110 includes a grill-like frame with horizontal and longitudinal rods 160, 180 to lift the patient.

Figure 3:
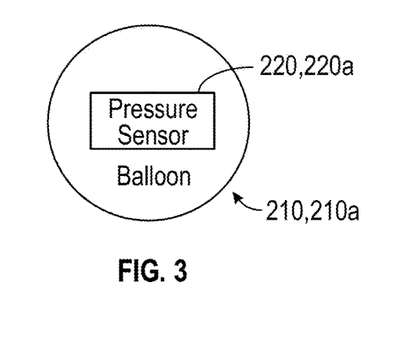
FIG. 3 is a block diagram illustrating an embodiment of a balloon and pressure sensor of the system of FIG. 1.

Horizontal and vertical rows of an array of expandable and collapsible supports such as, but not limited to inflatable air bladders/balloons 210 with pressure sensors/transducers 220, 220a (see FIG. 3) connected to inner lining of balloons 210 are carried by an underlying mattress foundation/box spring 225 of the movable support frame assembly 110. In an alternative embodiment, where there are no rods 160, 180 and corresponding assembly 110, the underlying mattress foundation/box spring 225 includes the emitters/holes 190, 200.

The balloons 210 are made of polyurethane foam and/or other materials, and their size can range from ultra-small to large. Ultra-small balloons have smaller pores for aeration/oxygenation in the interstitial spaces. These ultra-small and small balloons may be used for wheelchairs and other forms of resting chair/seating for disabled and chronically ill. The support frame assembly 110 preferably includes raised edges surrounding the array of balloon 210 to hold the balloons 210 in position and prevent the balloons 210 from moving outside of the bed/system 100. The array of balloons 210 form an unstitched mattress for the patient to rest on and allows for monitoring of pressure in each balloon 210 and adjustment of the air pressure in the balloon 210 as required. The horizontal rods 160, 180 lay within the array of balloons 210 to allow oxygenation and water jet massage of the back of the patient through interstitial spaces 228 between the balloons. The interstitial spaces 228 always remains open to oxygen flow even when the patient is resting on the balloons 210. The horizontal rods 160, 180 may be flat ribbon frame with soft velvet-like covering or cushioned frame to comfort the back of the patient when raised by lifting the rods 160, 180.

Actuators (e.g., pneumatic actuators) 230 vertically move the first support frame assembly 150 to move the horizontal rods 160 and the second support frame assembly 170 of the support frame assembly 110 to move the horizontal rods 180 for lifting/elevating the patient. The hinge points 140 on the support frame assembly 110 allow lifting of the torso or the lower extremities only. Alternatively, actuators 230 raise just the first support frame assembly 150 to move the horizontal rods 160 to clean the sections of the patient's back which would otherwise be covered by horizontal rods 180. This provides maximum exposure of the patient's back to clean/aerate and apply medication. Longitudinal spacing between these rods is optimized to allow comfortable resting of the patient only on support frame assembly 150. Alternatively, the system 100 includes a hammock-like mat (e.g., horizontal and vertical ropes of intertwined fibers) of ultra-strong fiber-like Kevlar or other high tension materials. The patient is lifted above the balloons 210 to lie in the hammock-like mat.

Figure 5:
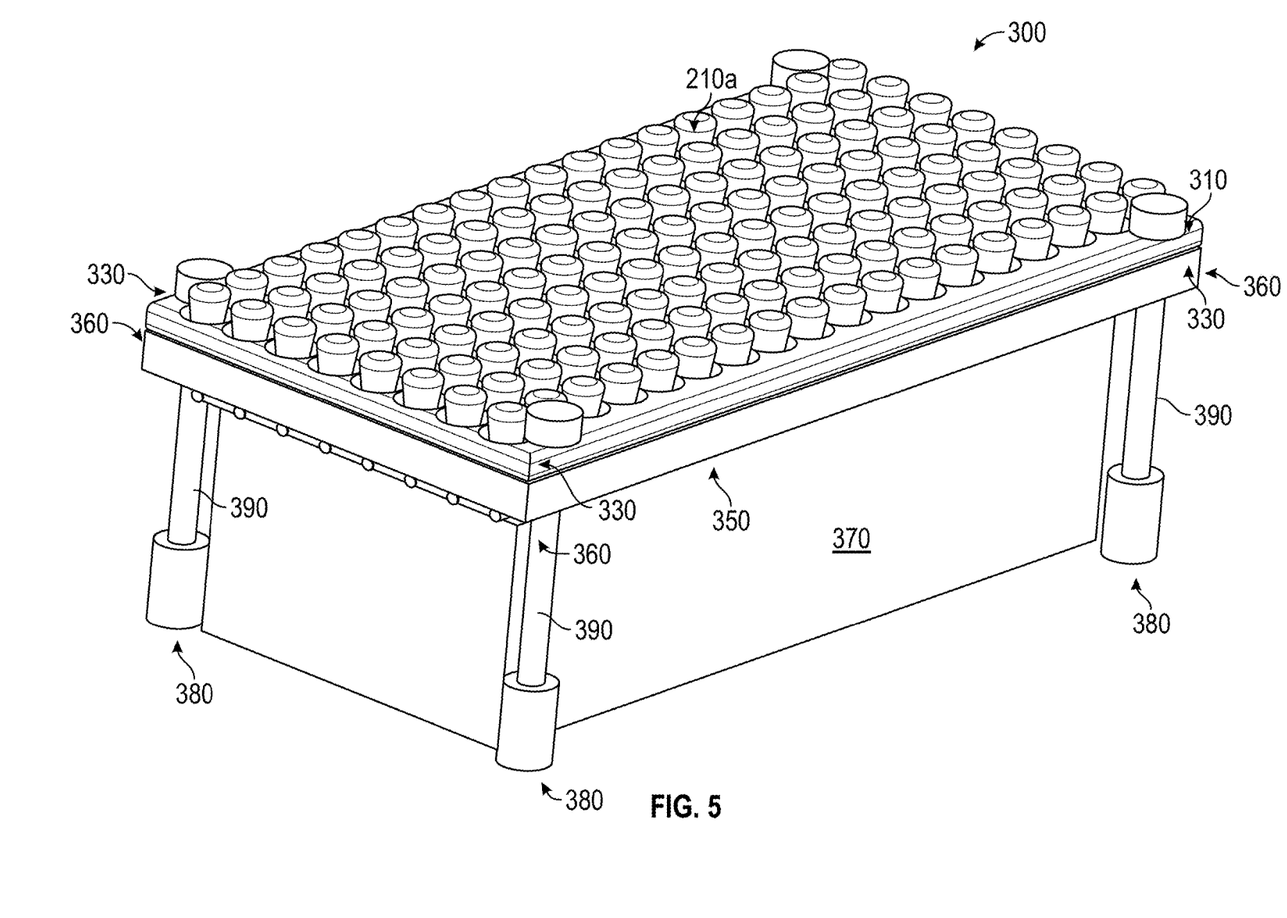
FIG. 5 is a perspective view of another embodiment of a system for treating and preventing pressure sores in bedridden patients and shows a top air-filled mattress in a lowered condition.
Figure 6:
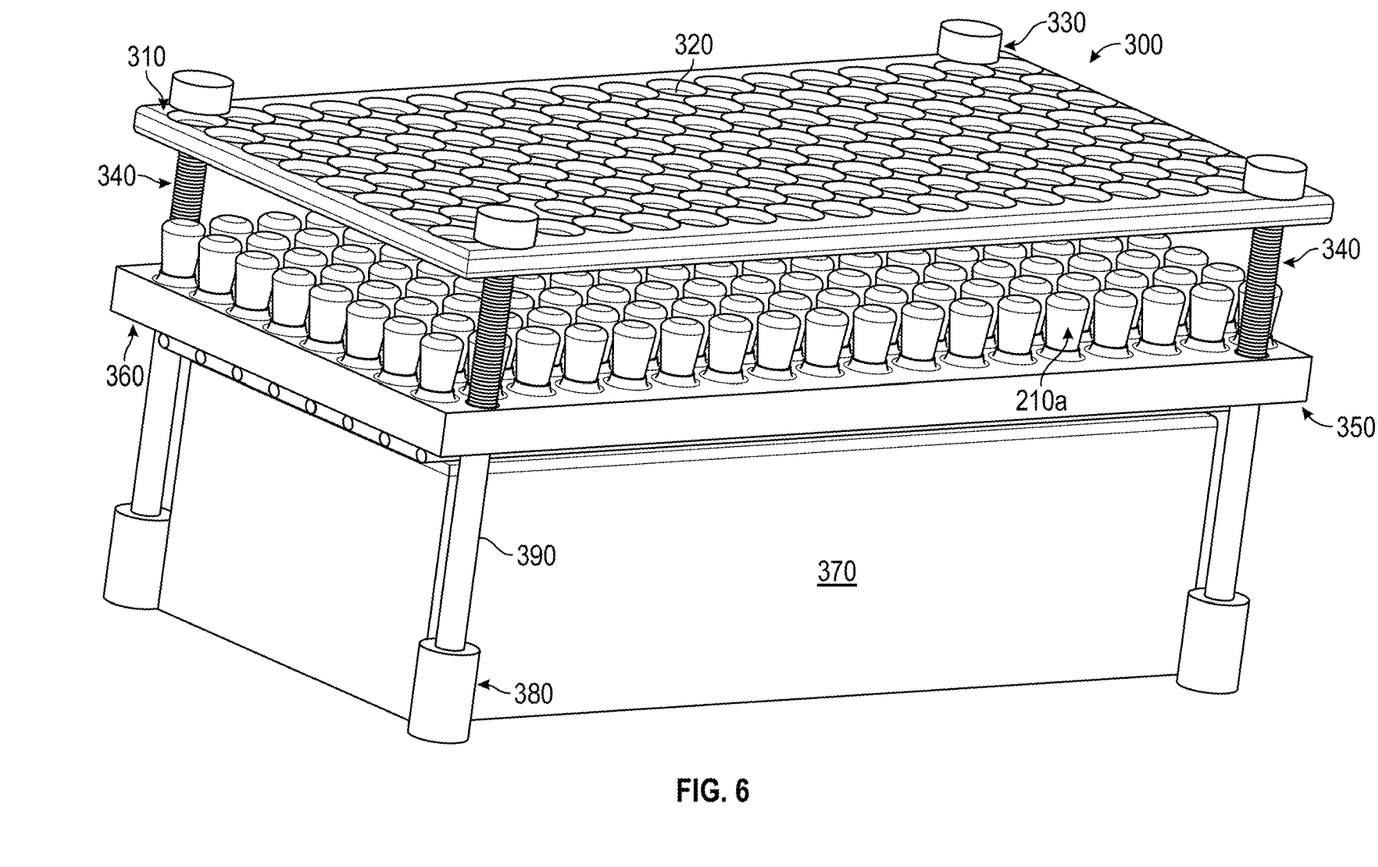
FIG. 6 is a perspective view of the system of FIG. 5 and shows a top air-filled mattress in a raised condition.
Figure 7:
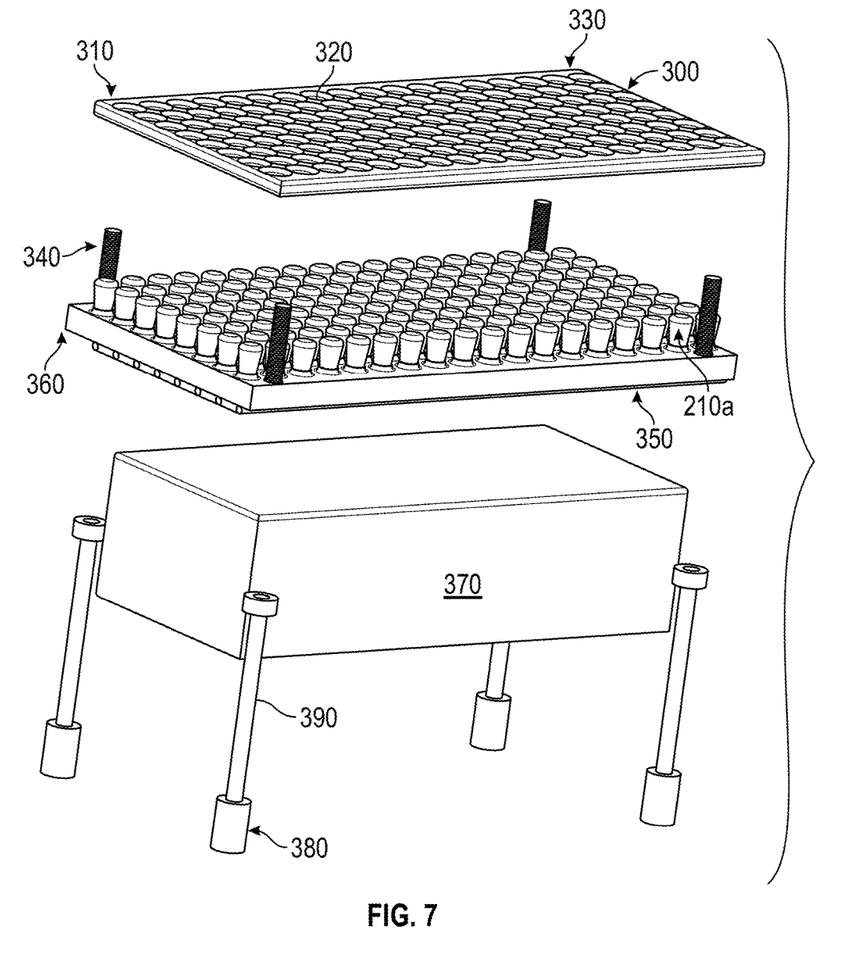
FIG. 7 is an exploded perspective view of the system of FIG. 5.

With reference to FIGS. 5-7, another embodiment of a therapeutic surface/system 300 will be described. Similar elements to those described above with respect to FIGS. 1-4 include a like element number and an "a" suffix. The therapeutic surface/system 300 includes a movable rectangular top air-filled mattress or patient lift 310 including horizontal and vertical rows of an array of circular holes 320 that respectively receive balloons 210a there through when the movable top air-filled mattress 310 is in the lowered position shown in FIG. 5. At four corner locations 330 of the top mattress 310, the top mattress 310 is supported by four respective counter-acting springs 340. The counter-acting springs 340 may be tension or compression springs. Although given that the patient lift for top mattress 310 will be required for only a short duration for cleaning of the patient's back, tension springs are preferred for springs 340 to minimize the energy consumption of actuators 380 as they will have to be working for smaller duration only when required to clean patient's back, compared to when using compression springs which will consume more energy to keep the top mattress 310 at the same level as the balloons 210.

A rectangular bottom air filled mattress 350 carries horizontal and vertical rows of an array of expandable and collapsible supports (e.g., inflatable balloons) 210a with pressure sensors/transducers 220a (see FIG. 3) connected to inner lining of balloons 210a to provide pressure monitoring and redistribution ability.

In the embodiment shown, the system 300 does not emit oxygen/water. However, in an alternative embodiment, the rectangular bottom air filled mattress 350 includes emitters/ holes provide in interstitial spaces between the balloons 210a to allow oxygenation and water jet massage of the back of the patient.

The balloons 210a are made of polyurethane foam and/or other materials, and their size can range from ultra-small to large. Ultra-small and small balloons 210a may be used for wheelchairs and other forms of resting chair/seating for disabled and chronically ill. The array of balloons 210a form an unstitched mattress for the patient to rest on and allows for monitoring of pressure in each balloon 210a and adjustment of the air pressure in the balloon 210a as required.

Figure 8:
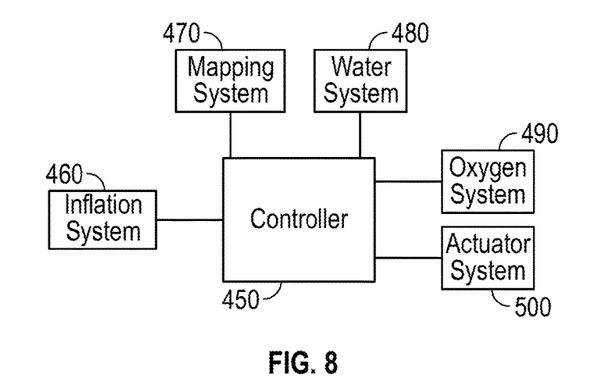
FIG. 8 is a block diagram of a control system of the respective systems of FIGS. 1-2 and 5-7.

The plurality of vertically oriented balloons 210a support the user, and the plurality of pressure sensors 220a are located beneath the vertically oriented balloons 210a. A series of pneumatic valve controls, integrated electronics, and sensory and control algorithms forming mapping system 470 and inflation system 460 in FIG. 8 are used to automatically sense the positioning of the patient upon the balloons 210a and to control and adjust the pressure within the balloons 210a. This is done, for example, by reducing the air in one or more balloons 210a, increasing in one or more balloons 210a, or maintaining the current amount of airy in one or more balloons 210a, depending on the patient's position and/or the weight detected by the various pressure sensors 220a.

At four corner locations 360 of the bottom mattress 350, the four respective counter-acting springs 340 are disposed for supporting the top mattress 310. The springs 340 can be actuated to keep the top mattress 310 upward.

A rectangular bed frame (e.g., at home, hospice, hospital) 370 supports the bottom mattress 350.

Actuators (e.g., pneumatic actuators) 380 vertically and individually move four posts 390, allowing the springs 340 to lift/move/raise the patient via the top mattress 310. As shown in FIG. 6, the top mattress 310 may be raised to clean the patient's back.

In use, the top mattress 310 is raised from the position shown in FIG. 5 to the position above the balloons 210a shown in FIG. 6 to alleviate pressure from the balloons 210a and/or to assist in keeping the skin clean and/or dried. The actuators 380 are controlled to move the posts 390 upward, allowing the springs 340 to lift/move/raise the patient upward via the top mattress 310 above and out of contact with the balloons 210a. The plurality of circular holes 320 move upward with the raising of the top mattress 310, around and over the balloons 210a. In this raised position, medication and/or wound care may be applied to the patient.

The top mattress 310 may be lowered to the position shown in FIG. 5, enabling the array of balloons 210a to provide pressure redistribution capability and alternating pressure points, preventing pressure sores. As the top mattress 310 is lowered, the plurality of circular holes 320 move downward with the lowering top mattress 310, around and over the balloons 210a so that in the position shown in FIG. 5 the balloons 210a extend vertically upward, out of the circular holes 320 (i.e., balloons 210a are positioned through the plurality of circular holes 320 when the lifting mechanisms is lowered).

The top mattress 310 can be a thin/skinny mattress, where the inter-circular area between the plurality of holes is minimized, thereby minimizing the contact area of the top mattress 310 with the patient's back. This way the patient is primarily resting on the balloons 210a and when the top mattress 310 is used to lift the patient, the top mattress 310 provides maximum exposure of the patient's back to clean/aerate and apply medication. The balloons 210a touch adjacent balloons 210a on all balloon-facing sides upon inflation so that the balloons 210a together make a nice puffed contiguous mattress except that the puffs are unstitched unlike in a typical mattress. When the balloons 210a are slightly deflated, they don't touch adjacent balloons 210a and, therefore, allow easy lifting of the top mattress/patient lift 310.

As shown in FIG. 6, the top mattress 310 can be significantly above the balloons 210a like 10" to 12" to allow cleaning the patient's back or reaching patient's back to apply medications, sponge bath, or aerate/oxygenate the back of the patient body.

Figure 11:
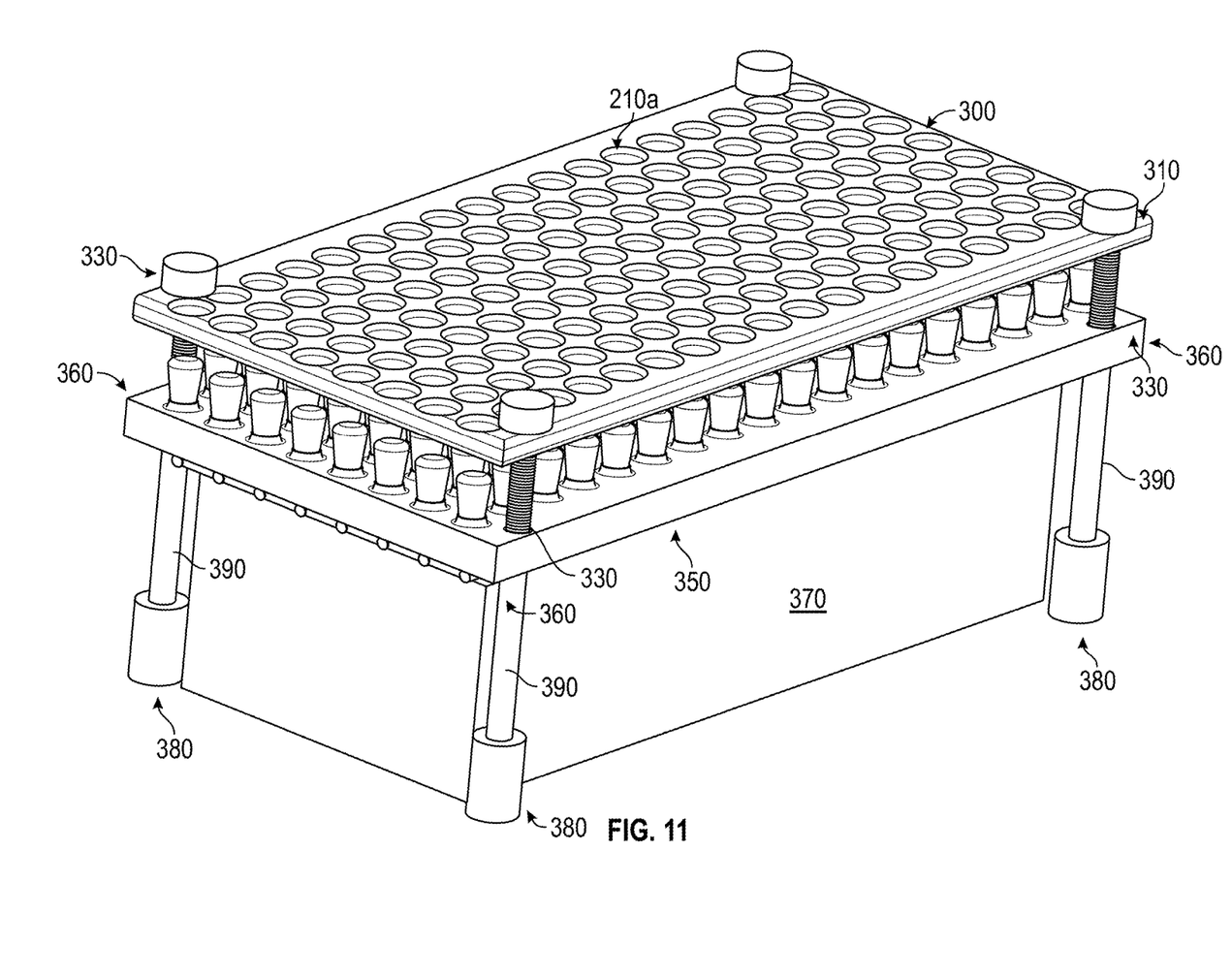
FIG. 11 is a perspective view of the system of FIG. 5 and shows a top air-filled mattress in a raised condition.

Alternately, as shown in FIG. 11, the top mattress 310 can be elevated only 0.25" to 2" above the balloons 210a, just enough to relieve the pressure points without balloon pressure alterations.

Figure 10:
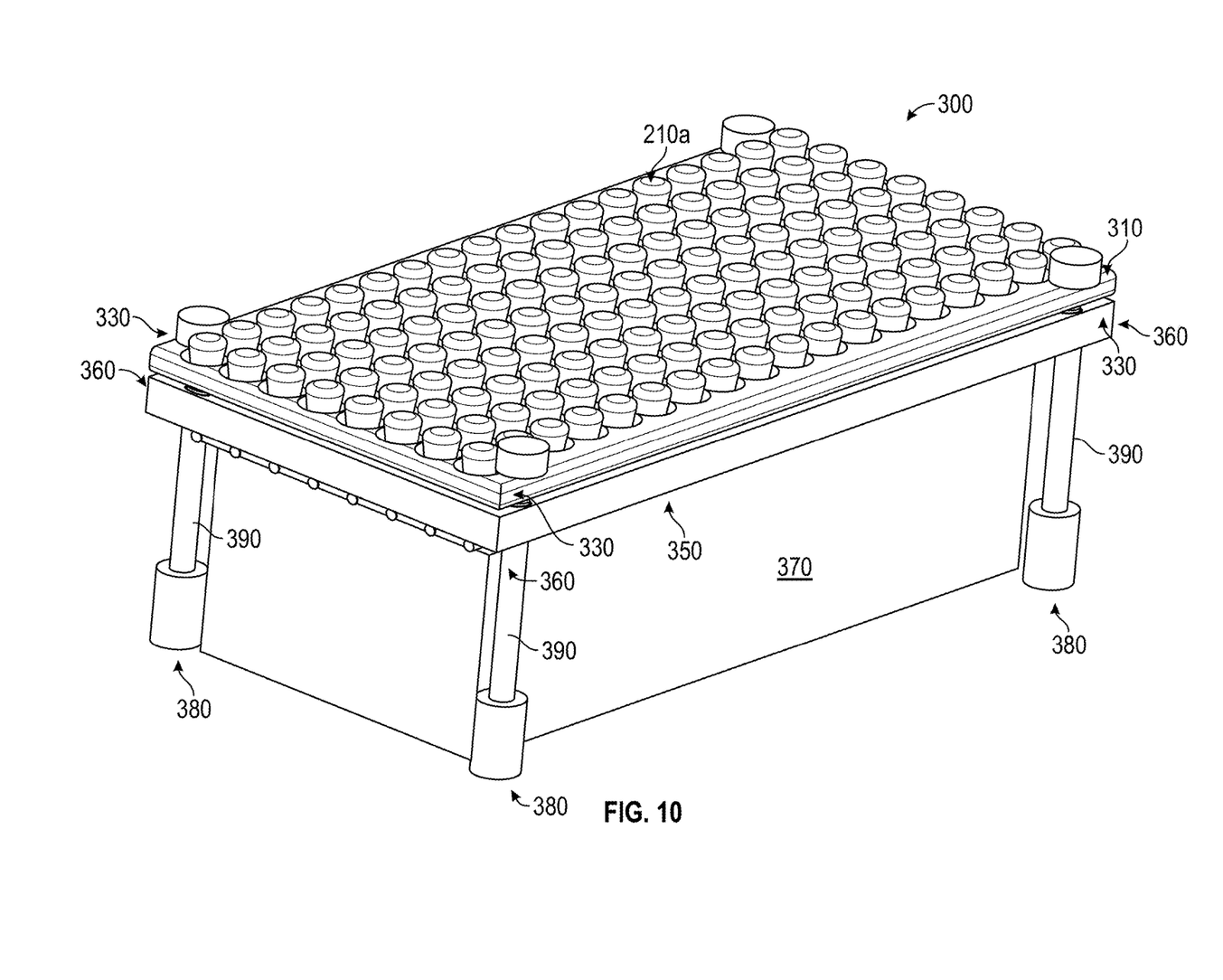
FIG. 10 is a perspective view of the system of FIG. 5 and shows a top air-filled mattress in a lowered condition.

As shown in FIG. 10, the top mattress can also be lowered by 0.25" to 2" below the top of the balloons 210a, just enough to alternate the pressure points. The top mattress 310 can be even with the balloons 210a when maximum comfort is desired—although maximum comfort is subjective and may be achieved in other positions with the top mattress 310 raised slightly above or below the balloons 210a.

Figure 12:
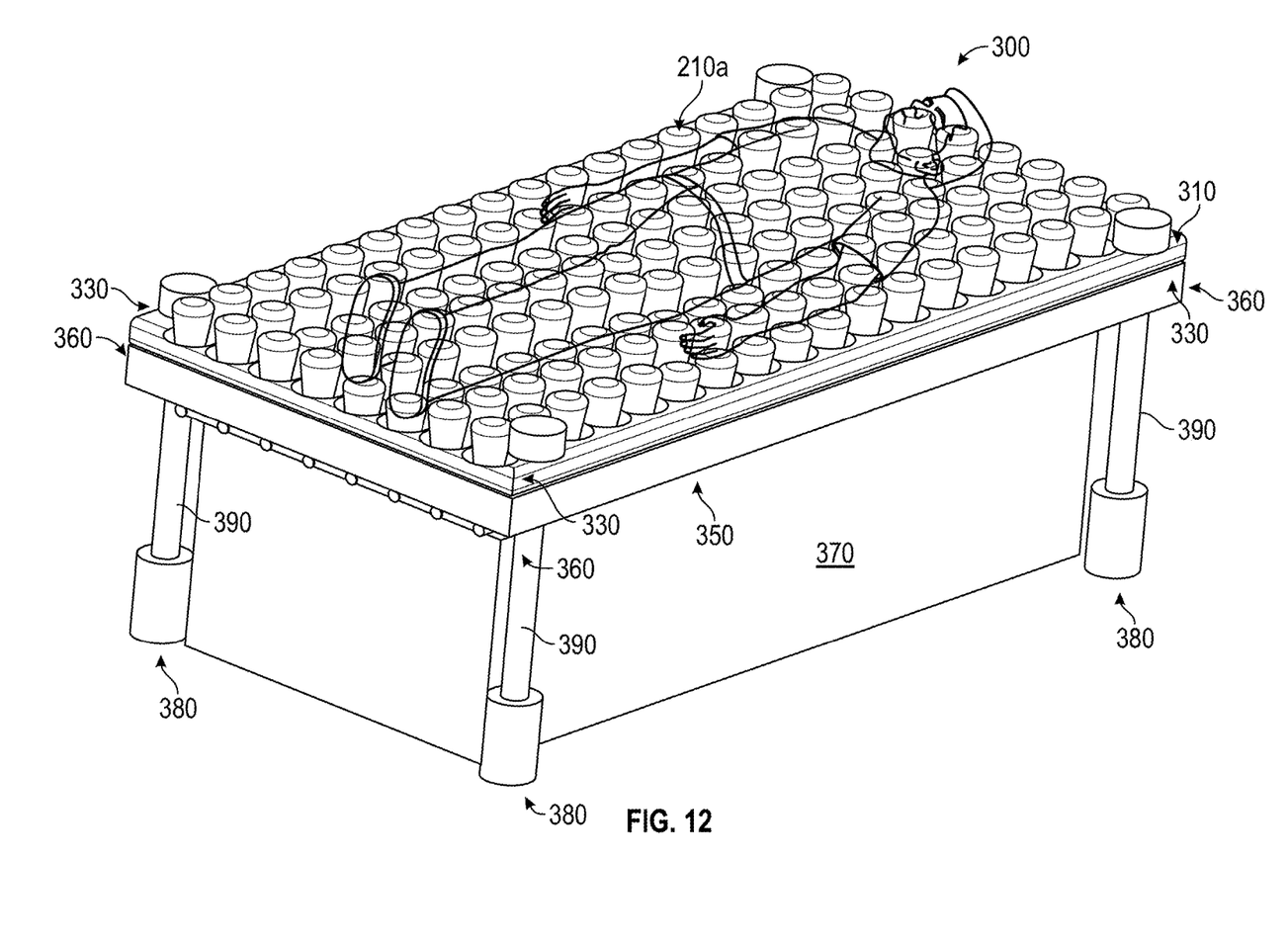
FIG. 12 is a perspective view of the system of FIG. 5 and shows a top air-filled mattress in a lowered condition with a patient shown thereon.

FIG. 12 shows the balloons 210a in a deflated condition under the head, in the sacral area (above the buttocks), under the elbows, ankle and heels relieving pressures in these sensitive areas prone to pressure sores due to thin skin/bony areas.

The top mattress 310 with plurality of holes 320 filled by the balloons 210a can be covered with a bed sheet or quilt as desired by the patient to feel comfortable like in their home bed.

The system 300 is a simple device preventing bed sores and reducing healthcare costs. Advantages of the system 300 include alternating pressure points preventing pressure sores, pressure redistribution capability, ability to alleviate pressure fully, keeps skin clean and dry, and allows application of medication and wound care.

With reference to FIG. 8, the system 100, 300 includes a controller 450, an inflation system 460, a pressure mapping system 470, a water/irrigation system 480 (alternative embodiment in the system 300), an oxygen system 490 (alternative embodiment in the system 300), and an actuator system 500.

The inflation system 460 is controlled by the controller 450 to adjust the air pressure in each balloon 210, 210a in order to adjust the amount of support pressure provided by each of the balloons 210, 210a to the patient. The inflation system 460 may include one or more inflation devices (e.g., compressor(s)), one or more inflation tubes, one or more valves, one or more manifolds, and/or one or more other inflation-related connectors/mechanisms to individually control the air pressure in each balloon 210, 210a.

The pressure mapping system 470 is controlled by the controller 450 to monitor the air pressure in each balloon 210, 210a through the pressure sensor(s) 220, 220a and cooperates with the inflation system to allow pressure adjustments of the air pressure in each balloon 210, 210a, as required. In an alternative embodiment, the inflation system 460 and the pressure mapping system 470 collectively form a single mapping/pressure system.

The water system 280a is controlled by the controller 450 to massage and/or clean the patient's back. Water from a water source is emitted under pressure out of the water holes/jets 180 to massage the patient's back/rear side in the embodiment of the system of FIGS. 1-2. As indicated above, the embodiment of the system 300 shown and described with respect to FIGS. 5-7 does not include a water system, but may include a water system in an alternative embodiment.

The oxygen system 490 is controlled by the controller 450 to oxygenate/aerate the patient's back/rear side. Oxygen/air from an oxygen/air source is emitted under pressure out of the oxygen holes 160 and onto the patient's back/rear side. As indicated above, the embodiment of the system 300 shown and described with respect to FIGS. 5-7 does not include an oxygen/air system, but may include an oxygen system in an alternative embodiment.

In the system 100, the actuator system 500 is controlled by the controller 450 to cause the pneumatic actuators 230 to vertically move the outer support frame assembly 150 and/or the inner support frame assembly 170 to move the horizontal rods 160, 180 for lifting/elevating the patient. The hinge points 140 on the support frame assembly 110 allow lifting of just the torso, just the lower extremities, and/or the patient's entire body (e.g., to clean the patient's back). This requires deflating the balloons 210 to lower pressures in the respective areas (torso/lower extremities/entire body), so that the lift can be raised at an angle pivoted by the hinges.

In the system 300, the actuator system 500 is controlled by the controller 450 to cause the pneumatic actuators 380 to vertically and individually move the four posts 390, allowing the springs 340 to lift/move/raise the patient via the top mattress 310. In an alternative embodiment of system 300 (not shown), hinge points on the patient lift similar to the one above (in system 100) allow lifting of just the torso, just the lower extremities, and/or the patient's entire body (e.g., to clean/aerate the patient's back or allow relieving pressures in desired areas). This will require to deflate the balloons 210 to lower pressures in the respective areas (torso/lower extremities/entire body), so that the lift can be raised at an angle pivoted by the hinges.

Figure 9:
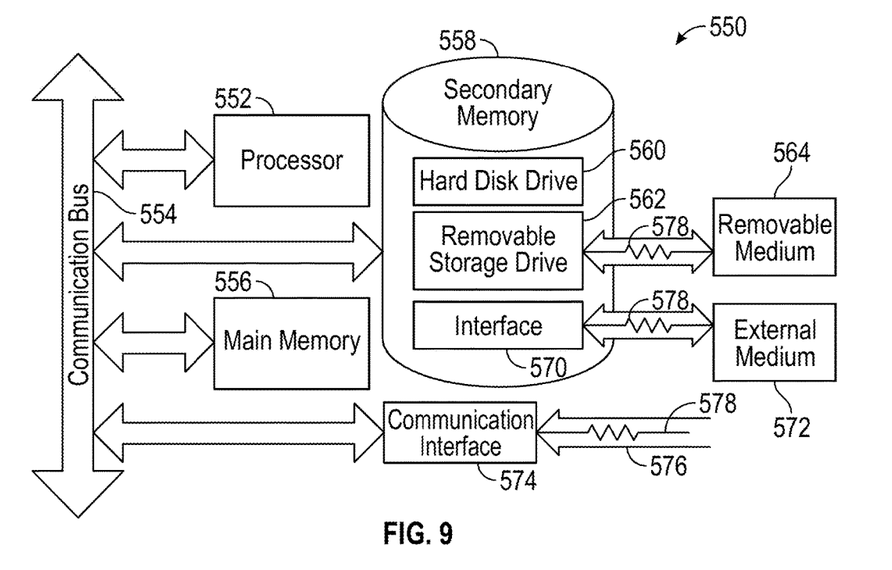
FIG. 9 is a block diagram illustrating an example computer system that may be used in connection with various embodiments described herein.

FIG. 9 is a block diagram illustrating an example computer system 550 that may be used in connection with various embodiments described herein such as the controller 450 in connection with the inflation system 460, the pressure mapping system 470, the water/irrigation system 280a, the oxygen system 490, and/or the actuator system 500. However, other computer systems and/or architectures may be used, as will be clear to those skilled in the art.

The computer system 550 preferably includes one or more processors, such as processor 552. Additional processors may be provided, such as an auxiliary processor to manage input/output, an auxiliary processor to perform floating point mathematical operations, a special-purpose microprocessor having an architecture suitable for fast execution of signal processing algorithms (e.g., digital signal processor), a slave processor subordinate to the main processing system (e.g., back-end processor), an additional microprocessor or controller for dual or multiple processor systems, or a coprocessor. Such auxiliary processors may be discrete processors or may be integrated with the processor 552.

The processor 552 is preferably connected to a communication bus 554. The communication bus 554 may include a data channel for facilitating information transfer between storage and other peripheral components of the computer system 550. The communication bus 554 further may provide a set of signals used for communication with the processor 552, including a data bus, address bus, and control bus (not shown). The communication bus 554 may comprise any standard or non-standard bus architecture such as, for example, bus architectures compliant with industry standard architecture ("ISA"), extended industry standard architecture ("EISA"), Micro Channel Architecture ("MCA"), peripheral component interconnect ("PCI") local bus, or standards promulgated by the Institute of Electrical and Electronics Engineers ("IEEE") including IEEE 488 general-purpose interface bus ("GPIB"), IEEE 696/S-100, and the like.

Computer system 550 preferably includes a main memory 556 and may also include a secondary memory 558. The main memory 556 provides storage of instructions and data for programs executing on the processor 552. The main memory 556 is typically semiconductor-based memory such as dynamic random access memory ("DRAM") and/or static random access memory ("SRAM"). Other semiconductor-based memory types include, for example, synchronous dynamic random access memory ("SDRAM"), Rambus dynamic random access memory ("RDRAM"), ferroelectric random access memory ("FRAM"), and the like, including read only memory ("ROM").

The secondary memory 558 may optionally include a hard disk drive 560 and/or a removable storage drive 562, for example a floppy disk drive, a magnetic tape drive, a compact disc ("CD") drive, a digital versatile disc ("DVD") drive, etc. The removable storage drive 562 reads from and/or writes to a removable storage medium 564 in a well-known manner. Removable storage medium 564 may be, for example, a floppy disk, magnetic tape, CD, DVD, etc.

The removable storage medium 564 is preferably a computer readable medium having stored thereon computer executable code (i.e., software) and/or data. The computer software or data stored on the removable storage medium 564 is read into the computer system 550 as electrical communication signals 578.

In alternative embodiments, secondary memory 558 may include other similar means for allowing computer programs or other data or instructions to be loaded into the computer system 550. Such means may include, for example, an external storage medium 572 and an interface 570. Examples of external storage medium 572 may include an external hard disk drive or an external optical drive, or and external magneto-optical drive.

Other examples of secondary memory 558 may include semiconductor-based memory such as programmable read-only memory ("PROM"), erasable programmable read-only memory ("EPROM"), electrically erasable read-only memory ("EEPROM"), or flash memory (block oriented memory similar to EEPROM). Also included are any other removable storage units 572 and interfaces 570, which allow software and data to be transferred from the removable storage unit 572 to the computer system 550.

Computer system 550 may also include a communication interface 574. The communication interface 574 allows software and data to be transferred between computer system 550 and external devices (e.g. printers), networks, or information sources. For example, computer software or executable code may be transferred to computer system 550 from a network server via communication interface 574. Examples of communication interface 574 include a modem, a network interface card ("NIC"), a communications port, a PCMCIA slot and card, an infrared interface, and an IEEE 1394 fire-wire, just to name a few.

Communication interface 574 preferably implements industry promulgated protocol standards, such as Ethernet IEEE 802 standards, Fiber Channel, digital subscriber line ("DSL"), asynchronous digital subscriber line ("ADSL"), frame relay, asynchronous transfer mode ("ATM"), integrated digital services network ("ISDN"), personal communications services ("PCS"), transmission control protocol/Internet protocol ("TCP/IP"), serial line Internet protocol/ point to point protocol ("SLIP/PPP"), and so on, but may also implement customized or non-standard interface protocols as well.

Software and data transferred via communication interface 574 are generally in the form of electrical communication signals 578. These signals 578 are preferably provided to communication interface 574 via a communication channel 576. Communication channel 576 carries signals 578 and can be implemented using a variety of wired or wireless communication means including wire or cable, fiber optics, conventional phone line, cellular phone link, wireless data communication link, radio frequency (RF) link, or infrared link, just to name a few.

Computer executable code (i.e., computer programs or software) is stored in the main memory 556 and/or the secondary memory 558. Computer programs can also be received via communication interface 574 and stored in the main memory 556 and/or the secondary memory 558. Such computer programs, when executed, enable the computer system 550 to perform the various functions of the present invention as previously described.

In this description, the term "computer readable medium" is used to refer to any media used to provide computer executable code (e.g., software and computer programs) to the computer system 550. Examples of these media include main memory 556, secondary memory 558 (including hard disk drive 560, removable storage medium 564, and external storage medium 572), and any peripheral device communicatively coupled with communication interface 574 (including a network information server or other network device). These computer readable mediums are means for providing executable code, programming instructions, and software to the computer system 550.

In an embodiment that is implemented using software, the software may be stored on a computer readable medium and loaded into computer system 550 by way of removable storage drive 562, interface 570, or communication interface 574. In such an embodiment, the software is loaded into the computer system 550 in the form of electrical communication signals 578. The software, when executed by the processor 552, preferably causes the processor 552 to perform the inventive features and functions previously described herein.

Various embodiments may also be implemented primarily in hardware using, for example, components such as application specific integrated circuits ("ASICs"), or field programmable gate arrays ("FPGAs"). Implementation of a hardware state machine capable of performing the functions described herein will also be apparent to those skilled in the relevant art. Various embodiments may also be implemented using a combination of both hardware and software.

Furthermore, those of skill in the art will appreciate that the various illustrative logical blocks, modules, circuits, and method steps described in connection with the above described figures and the embodiments disclosed herein can often be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a module, block, circuit or step is for ease of description. Specific functions or steps can be moved from one module, block or circuit to another without departing from the invention.

Moreover, the various illustrative logical blocks, modules, and methods described in connection with the embodiments disclosed herein can be implemented or performed with a general purpose processor, a digital signal processor ("DSP"), an ASIC, FPGA or other programmable logic device, discrete gate or transistor logic, discrete hardware components, or any combination thereof designed to perform the functions described herein. A general-purpose processor can be a microprocessor, but in the alternative, the processor can be any processor, controller, micro controller, or state machine. A processor can also be implemented as a combination of computing devices, for example, a combination of a DSP and a microprocessor, a plurality of microprocessors, one or more microprocessors in conjunction with a DSP core, or any other such configuration.

Additionally, the steps of a method or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of storage medium including a network storage medium. An exemplary storage medium can be coupled to the processor such the processor can read information from, and write information to, the storage medium. In the alternative, the storage medium can be integral to the processor. The processor and the storage medium can also reside in an ASIC.

The above figures may depict exemplary configurations for the invention, which is done to aid in understanding the features and functionality that can be included in the invention. The invention is not restricted to the illustrated architectures or configurations, but can be implemented using a variety of alternative architectures and configurations. Additionally, although the invention is described above in terms of various exemplary embodiments and implementations, it should be understood that the various features and functionality described in one or more of the individual embodiments with which they are described, but instead can be applied, alone or in some combination, to one or more of the other embodiments of the invention, whether or not such embodiments are described and whether or not such features are presented as being a part of a described embodiment. Thus the breadth and scope of the present invention, especially in the following claims, should not be limited by any of the above-described exemplary embodiments.

Terms and phrases used in this document, and variations thereof, unless otherwise expressly stated, should be construed as open ended as opposed to limiting. As examples of the foregoing: the term "including" should be read as mean "including, without limitation" or the like; the term "example" is used to provide exemplary instances of the item in discussion, not an exhaustive or limiting list thereof; and adjectives such as "conventional," "traditional," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although item, elements or components of the disclosure may be described or claimed in the singular, the plural is contemplated to be within the scope thereof unless limitation to the singular is explicitly stated. The presence of broadening words and phrases such as "one or more," "at least," "but not limited to" or other like phrases in some instances shall not be read to mean that the narrower case is intended or required in instances where such broadening phrases may be absent.

I claim:

1. A system for preventing and treating pressure sores of a patient, comprising:
   an array of expandable and collapsible supports to support and provide pressure relief to a patient in pressure locations where the expandable and collapsible supports support the patient;
   pressure sensors associated with the expandable and collapsible supports to monitor pressure locations where the expandable and collapsible supports support the patient;
   a patient lift movable between the expandable and collapsible supports to raise and lower the patient between at least a position where the patient is primarily supported by the array of expandable and collapsible supports and a position above the expandable and collapsible supports where the patient is primarily supported by the patient lift,
   wherein the array of expandable and collapsible supports include interstitial spaces between the expandable and collapsible supports, and one or more emitters are disposed in the interstitial spaces, the one or more emitters include one or more of air emitters, oxygen emitters, and water emitters.

2. The system of claim 1, wherein the patient lift includes a plurality of holes, one hole per expandable and collapsible support, that the expandable and collapsible supports are respectively disposed within when the patient lift is raised and lowered.

3. The system of claim 2, wherein the patient lift is a top mattress.

4. The system of claim 3, wherein the patient lift is an air-filled mattress.

5. The system of claim 1, wherein the system is integrated into a hospital bed.

6. The system of claim 1, wherein the system is a seat that is a member of the group consisting of wheel chair seating, seats in automobiles, seats in airplanes, workplace seats in factories, workplace seats in offices, and back massage chairs.

7. The system of claim 1, wherein the lift includes multiple actuators operably associated with the patient lift to raise and lower the patient lift.

8. The system of claim 1, further including a bottom air filled mattress with the array of expandable and collapsible supports.

9. The system of claim 1, wherein the expandable and collapsible supports are inflatable balloons.

10. The system of claim 9, wherein pressure sensors are respectively associated with the inflatable balloons, and further including a controller operably associated with the pressure sensors and the inflatable balloons to control the inflation of the inflatable balloons based on the sensed pressure by the pressure sensors to prevent pressure sores.

11. A system for preventing and treating pressure sores of a patient, comprising:
   an array of expandable and collapsible supports to support and provide pressure relief to a patient in pressure locations where the expandable and collapsible supports support the patient;
   pressure sensors associated with the expandable and collapsible supports to monitor pressure locations where the expandable and collapsible supports support the patient;
   a patient lift movable between the expandable and collapsible supports to elevate one or more areas of the patient, the patient lift including one or more air emitters, oxygen emitters, and water emitters to aerate one or more areas of the patient, oxygenate one or more areas of the patient, and/or rinse one or more areas of the patient,
   wherein the array of expandable and collapsible supports include interstitial spaces between the expandable and collapsible supports and the one or more emitters are disposed in the interstitial spaces.

12. The system of claim 11, wherein the expandable and collapsible supports provide pressure relief and the one or more emitters provide aeration, oxygenation, and/or rinsing without elevating the patient with the patient lift.

13. The system of claim 11, wherein the lift includes one or more hinges, enabling the lift to lift the patient's torso alone, the patient's lower extremities alone, or the patient's entire body.

14. The system of claim 11, wherein the expandable and collapsible supports touch adjacent expandable and collapsible supports on all sides upon expansion so that the array of expandable and collapsible supports make a contiguous mattress except that the expandable and collapsible supports are unstitched.

15. A system for preventing and treating pressure sores of a patient, comprising:
   an array of expandable and collapsible supports to support and provide pressure relief to a patient in pressure locations where the expandable and collapsible supports support the patient;
   pressure sensors associated with the expandable and collapsible supports to monitor pressure locations where the expandable and collapsible supports support the patient;
   a patient lift movable between the expandable and collapsible supports to elevate one or more areas of the patient, the patient lift including one or more air emitters, oxygen emitters, and water emitters to aerate one or more areas of the patient, oxygenate one or more areas of the patient, and/or rinse one or more areas of the patient, wherein the lift includes horizontal supports disposed between the expandable and collapsible supports, and the horizontal supports include the one or more emitters.

16. The system of claim 15, wherein the expandable and collapsible supports touch adjacent expandable and collapsible supports on all sides upon expansion so that the array of expandable and collapsible supports make a contiguous mattress except that the expandable and collapsible supports are unstitched.

* * * * *